(12) United States Patent
Minakata et al.

(10) Patent No.: US 7,381,706 B2
(45) Date of Patent: Jun. 3, 2008

(54) GONADOTROPIN-RELEASING HORMONE, PRECURSOR PEPTIDES THEREOF AND GENES ENCODING THE SAME

(75) Inventors: Hiroyuki Minakata, Kawabe-gun (JP); Eiko Iwakoshi, Kashiwara (JP); Kyoko Kuroda, Kyoto (JP)

(73) Assignee: Suntory Limited, Osaka-shi (JP)

( * ) Notice: Subject to any disclaimer, the term of this patent is extended or adjusted under 35 U.S.C. 154(b) by 876 days.

(21) Appl. No.: 10/312,637

(22) PCT Filed: Jun. 29, 2001

(86) PCT No.: PCT/JP01/05607

§ 371 (c)(1),
(2), (4) Date: Dec. 30, 2002

(87) PCT Pub. No.: WO02/02628

PCT Pub. Date: Jan. 10, 2002

(65) Prior Publication Data

US 2005/0143567 A1    Jun. 30, 2005

(30) Foreign Application Priority Data

Jun. 30, 2000    (JP)    ............................. 2000-198430

(51) Int. Cl.
*A01K 67/033*    (2006.01)
*A61K 38/10*    (2006.01)
*C07K 14/575*    (2006.01)

(52) U.S. Cl. ........................ 514/14; 119/234; 530/313; 530/327; 530/857

(58) Field of Classification Search ...................... None
See application file for complete search history.

(56) References Cited

U.S. PATENT DOCUMENTS 5,075,224 A * 12/1991 Seeburg et al. ............ 435/69.4

FOREIGN PATENT DOCUMENTS

EP    0 145 258 A1    6/1985
WO    WO 96/40757 A2    12/1996

OTHER PUBLICATIONS

Iwakoshi et al. Isoation And Characterization Of A GnRH-Like Peptide From *Octopus vulgaris*. Zoological Science (Tokyo). Dec. 2000, vol. 17 (Supplement), p. 11.*

(Continued)

*Primary Examiner*—Jeffrey Edwin Russel
(74) *Attorney, Agent, or Firm*—Crowell & Moring LLP (57) ABSTRACT

A novel peptide found as gonadotropin-releasing hormone (GnRH) in octopuses, a member of mollusks. The structure and the activities of the peptide have been unraveled. The peptide finds use as a reagent used in the studies of correlations between the structure and the activities of GnRH and the information processing mechanisms of the nervous systems in higher animals. It can also serve as a base compound in the development of pesticides and drugs.

The peptide has the GnRH activity and has the following amino acid sequence (I):

$$<\text{Glu-Zaa-Zaa-His-Zaa-Ser-Zaa-Zaa-Zaa-Zaa-Pro-Gly-NH}_2 \text{ (SEQ ID NO: 7)} \quad (I)$$

wherein <Glu represents pyroglutamic acid and Zaa represents any amino acid. Specifically, the peptide has the following amino acid sequence (1):

$$<\text{Glu-Asn-Tyr-His-Phe-Ser-Asn-Gly-Trp-His-Pro-Gly-NH}_2 \text{ (SEQ ID NO: 1)} \quad (1)$$

wherein <Glu represents pyroglutamic acid.

9 Claims, 6 Drawing Sheets

Structural comparison of gonadotropin-releasing hormones

| | |
|---|---|
| Mammalian | pGlu-His-Trp-Ser-Tyr-Gly-Leu-Arg-Pro-Gly-NH$_2$ |
| Chicken I | pGlu-His-Trp-Ser-Tyr-Gly-Leu-Gln-Pro-Gly-NH$_2$ |
| Chicken II | pGlu-His-Trp-Ser-His-Gly-Trp-Tyr-Pro-Gly-NH$_2$ |
| Salmon | pGlu-His-Trp-Ser-Tyr-Gly-Trp-Leu-Pro-Gly-NH$_2$ |
| Lamprey I | pGlu-His-Tyr-Ser-Leu-Glu-Trp-Lys-Pro-Gly-NH$_2$ |
| Lamprey III | pGlu-His-Trp-Ser-His-Asp-Trp-Lys-Pro-Gly-NH$_2$ |
| Sea squirt I | pGlu-His-Trp-Ser-Asp-Tyr-Phe-Lys-Pro-Gly-NH$_2$ |
| Sea squirt II | pGlu-His-Trp-Ser-Leu-Cys-His-Ala-Pro-Gly-NH$_2$ |
| O. vulgaris | pGlu-Asn-Tyr-His-Phe-Ser-Asn-Gly-Trp-His-Pro-Gly-NH$_2$ |

OTHER PUBLICATIONS

Iwakoshi et al. Isolation and Characterization of a GnRH-Like Peptide from *Octopus vulgaris*. 14th International Congress of Comparative Endocrinology. Perspective in Comparative Endocrinology. May 26-30, 2001, pp. 585-590.*

T. L. Kasten, et al., "Characterization of two new preproGnRHmRNAs in the tree shrew: First direct evidence for mesencephalic GnRH gene expression in a placental mammel" Gen. Comp. Endocrinol., vol. 104, 1996, No. 1, pp. 7-19.

A. Di Cosmo, et al., "Neuropeptidergic control on the optic gland of *Octopus vulgaris*: FMRF-amide and GnRH immunoreactivity" Journal of Comparative Neurology, vol. 398, 1998, No. 1, pp. 1-12.

D. A. Lovejoy, et al., "Distinct sequence of gonadotropin-releasing hormone (GnRH) in dogfish brain provides insight into GnRH evolution" Proc. Natl. Acad. Science, USA, vol. 89, 1992, No. 14, pp. 6373-6377.

S. A. White, et al., "A second gene for gonadotropin-releasing hormone: cDNA and expression pattern in the brain" Proc. Natl. Acad. Science, USA, vol. 91, 1994, No. 4, pp. 1423-1427.

R. B. White, et al., "Second gene for gonadotropin-releasing hormone in humans" Proc. Natl. Acad. Science, USA, vol. 95, 1998. No. 1, pp. 305-309.

Iwakoshi et al., "Isolation and Characterization of a GnRH-like Peptide from *Octopus vulgaris*," Biochemical and Biophysical Research Communications, 2002, pp. 1187-1193, vol. 291, Elsevier Science, USA.

Database CA 'Online!, Chemical Abstracts Service, Columbus, OH, USA, Iwakoshi et al., "Isolation and characterization of a GnRH-like peptide from *Octopus vulgaris*," XP002351359, retrieved from STN Database accession No. 138:268612.

* cited by examiner

↑
Chicken II: $10^{-5}$ M

1g

3min (b)

↑
Compound (2): $10^{-5}$ M

Structural comparison of gonadotropin-releasing hormones

| | |
|---|---|
| Mammalian | pGlu-His-Trp-Ser-Tyr-Gly-Leu-Arg-Pro-Gly-NH$_2$ |
| Chicken I | pGlu-His-Trp-Ser-Tyr-Gly-Leu-Gln-Pro-Gly-NH$_2$ |
| Chicken II | pGlu-His-Trp-Ser-His-Gly-Trp-Tyr-Pro-Gly-NH$_2$ |
| Salmon | pGlu-His-Trp-Ser-Tyr-Gly-Trp-Leu-Pro-Gly-NH$_2$ |
| Lamprey I | pGlu-His-Tyr-Ser-Leu-Glu-Trp-Lys-Pro-Gly-NH$_2$ |
| Lamprey III | pGlu-His-Trp-Ser-His-Asp-Trp-Lys-Pro-Gly-NH$_2$ |
| Sea squirt I | pGlu-His-Trp-Ser-Asp-Tyr-Phe-Lys-Pro-Gly-NH$_2$ |
| Sea squirt II | pGlu-His-Trp-Ser-Leu-Cys-His-Ala-Pro-Gly-NH$_2$ |
| O. vulgaris | pGlu-Asn-Tyr-His-Phe-Ser-Asn-Gly-Trp-His-Pro-Gly-NH$_2$ |

Fig. 6

```
                           CTCTGAACAGCGTCCTGAACCTGATACATAG    31
AACAAACTCAAGTTCCACACTAAAGATCTAACTTATCCAATTCTACCAGCAAACGTCATT    91

ATGTCAGCTACTGCATCAACAACCAGCTCCAGAAAAATGGCTTTCTTCATATTCTCCATG   151
 M  S  A  T  A  S  T  T  S  S  R  K  M  A  F  F  I  F  S  M    20

TTGCTGCTATCTTTGTGTCTGCAGACTCAAGCACAAAACTACCACTTTAGCAATGGATGG   211
 L  L  L  S  L  C  L  Q  T  Q  A  Q  N  Y  H  F  S  N  G  W    40

CACCCCGGAGGTAAACGCAGTGCACTCTCAGACATTCAGTGTCACTTCAGACAACAAACA   271
 H  P  G  K  R  S  A  L  S  D  I  Q  C  H  F  R  Q  Q  T       60

AAGGCTTTGATAGAAAAAATTTTAGATGAAGAGATTAACCGTATTATCACAACATGTACC   331
 K  A  L  I  E  K  I  L  D  E  E  I  N  R  I  I  T  T  C  T    80

GGGCCGGTCAATGAGATTGCAGACCTATGAAAGATAGCATATACTTTGGAGAGAAATCCT   391
 G  P  V  N  E  I  A  D  L  *                                  89

GACTGGCAAAGATATCCCTTCCGACAAACACCAAGACCAATGACAATGATGATGACAACA   451
ACAATGATGATGATGAGAACGATAACTGCAATGAACGAGACTGATGACTCTCGTGTGGTG   511
TTTGGTCCTTCACATGGGTGGTGGGAGTGGTTACACAAAACAGAAAAAGAAAAAATACA    571
AATATTAAAAAGGGAGAGTAAAAAATGAAAAAAATCCCGTCTGAAACATGTCCACTTTA    631
ATGTATAATTAATTCATCAACTAATTAACTCGCCAATTAATTGTGCATCAGCTTAATGTC   691
TGTCCTTTGATAATCTCAGACAATGTTTTGTGGAATAAAATATTCGATCTCTGCCAAAAA   751
AAAAAAAAAAAAAAAAAAA                                            770
```

GONADOTROPIN-RELEASING HORMONE, PRECURSOR PEPTIDES THEREOF AND GENES ENCODING THE SAME

TECHNICAL FIELD

The present invention relates to a novel neuropeptide and, more particularly, to a novel peptide that is obtained from brains of *Octopus vulgaris* (including optic glands, optic tracts, and optic lobes) and has the gonadotropin-releasing hormone (GnRH) activity. The present invention also relates to a precursor polypeptide of such a peptide and a gene encoding the same.

BACKGROUND ART

Invertebrates have a complex endocrine system that has developed along with their nervous system. In invertebrates, various endogenous peptides are known that serve as neurotransmitters, neuromodulators or neurohormones.

Mollusks generally have a simpler nervous system as compared to higher animals. Their nervous systems therefore serve as a useful tool in studying the mechanisms of information processing. Any knowledge obtained at cellular level about the information processing mechanisms of mollusks is considered generally applicable to the information processing mechanisms of nervous systems of higher animals For this reason, a significant amount of effort has been made to find neurotransmitters of mollusks.

For example, an endogenous neuropeptide obtained from mussel is disclosed in Japanese Patent Laid-Open Publication No. Hei 1-221392. A novel peptide isolated from ganglia of *Achatina fulica* is disclosed in Japanese Patent Laid-Open Publication No. Hei 2-286696. This peptide includes a D-amino acid and is found to function as an endogenous neurotransmitter. Japanese Patent Laid-Open Publication No. 6-56890 discloses a neuropeptide isolated from ganglia of a Hungarian snail.

Aside from those described above, various other neuropeptides have been isolated from mollusks and have been identified. Examples include Ala-Pro-Gly-Trp-$NH_2$ (SEQ ID NO: 17), myomodulin-CARP, small cardioactive peptide (SCP), buccalin, and Phe-Met-Arg-Phe-$NH_2$ (SEQ ID NO: 18) (FMRF-amide)(M. Kobayashi and Y. Muneoka, *Zool. Sci.*, 7, 801 (1990); Y. Muneoka and M. Kobayashi, *Experimentia* 48, 448 (1992); Youjiro. Muneoka, *Journal of Pesticide Science* 18, 5191 (1993); Y. Muneoka, T. Takahashi, M. Kobayashi, "Perspective in Comparative Endocrinology", National Research Council of Canada, 1994, p109; A. Di Cosmo and C. Di Cristo, *J. Comp. Neurol.*, 398, 1-12 (1998)).

Mollusks form one of the largest families of invertebrates. Of different species of mollusks, octopuses belong to a group called Cephalopoda. The animals have highly developed brains and far more advanced motor and sensory functions than other members of mollusks. The neurosecretory system of octopuses has been extensively studied. In 1956, Boycott and Young discovered that cutting the optic tract of the animal results in enlarged optic glands and development of gonads. Later, the Wells showed that the gland secretes a gonadotropic hormone (M. J. Wells and J. Wells, *J. Exp. Biol.*, 36, 1-33 (1959)). It turned out that the hormone is a protein hormone and affects the growth of germ cells, the maturation of gonad-related organs, and the synthesis of yolk protein. The hormone is also involved in parenting behaviors of octopuses after their laying eggs (Atlas of endocrine organs, Japan Society for Comparative Endocrinology. ed., Kodansha).

Gonadotropin-releasing hormone (GnRH) was first isolated in 1971 by Schally et al., from the porcine hypothalamus and was then discovered as luteinizing hormone-releasing hormone (LHRH). Its structure was also determined. Since then GnRHs have been studied by many researchers. To date, many GnRHs have been found in different vertebrates such as mammals, birds, and salmon. Also, some suggest that many invertebrates include tissues and substances that are immunoreactive to GnRH (A. Di Cosmo and C. Di Cristo, *J. Comp. Neurol.*, 398, 1-12 (1998)).

It has been shown that, in mammals, GnRHs are secreted from hypothalamus and act on the pituitary gland to cause the release of gonadotropic hormones. These GnRHs are each a decapeptide.

In octopuses, however, the structure of the gonadotropic hormone has yet to be determined although it is known, as described above, that the gonadotropins are secreted from their optic glands. Moreover, no GnRH has yet been isolated from octopuses, nor has its structure been determined.

Accordingly, it is an objective of the present invention to identify, and determine the structure of, a novel GnRH of octopuses. It is another objective of the present invention to understand the activities of the GnRH, the structure of which is determined according to the present invention, both in octopuses and in other invertebrates and vertebrates.

A further objective of the present invention is to provide a novel peptide that can serve as a useful reagent in studying correlations between the structure and the activities of GnRH and in studying the information processing mechanisms of nervous systems in higher animals. A still further objective of the present invention is to provide a novel peptide that can be used as a base compound in the development of pesticides and drugs.

It is yet another objective of the present invention to identify a precursor polypeptide of the GnRH and a gene encoding the precursor for the purpose of expanding our knowledge about evolution of animals. It is yet another objective of the present invention to provide a method for producing the GnRH.

DISCLOSURE OF THE INVENTION

In an effort to isolate GnRH from octopuses, the present inventors conducted extensive studies on various physiologically active peptides obtained from the brains of about 100 specimens of *O. vulgaris* by investigating the activities of the peptides to enhance the heart beat of the animals. As a result, the present inventors isolated and purified a peptide having the following amino acid sequence (1), determined its structure, and verified the structure by total synthesis:

<Glu-Asn-Tyr-His-Phe-Ser-Asn-Gly-Trp-His-Pro-Gly-$NH_2$ (SEQ ID NO: 1)    (1)

wherein <Glu represents pyroglutamic acid. This peptide may be referred to as Compound (1), hereinafter. Unless specified, all amino acids are represented by the three-letter codes defined by the IUPAC nomenclature system.

Figure 5:
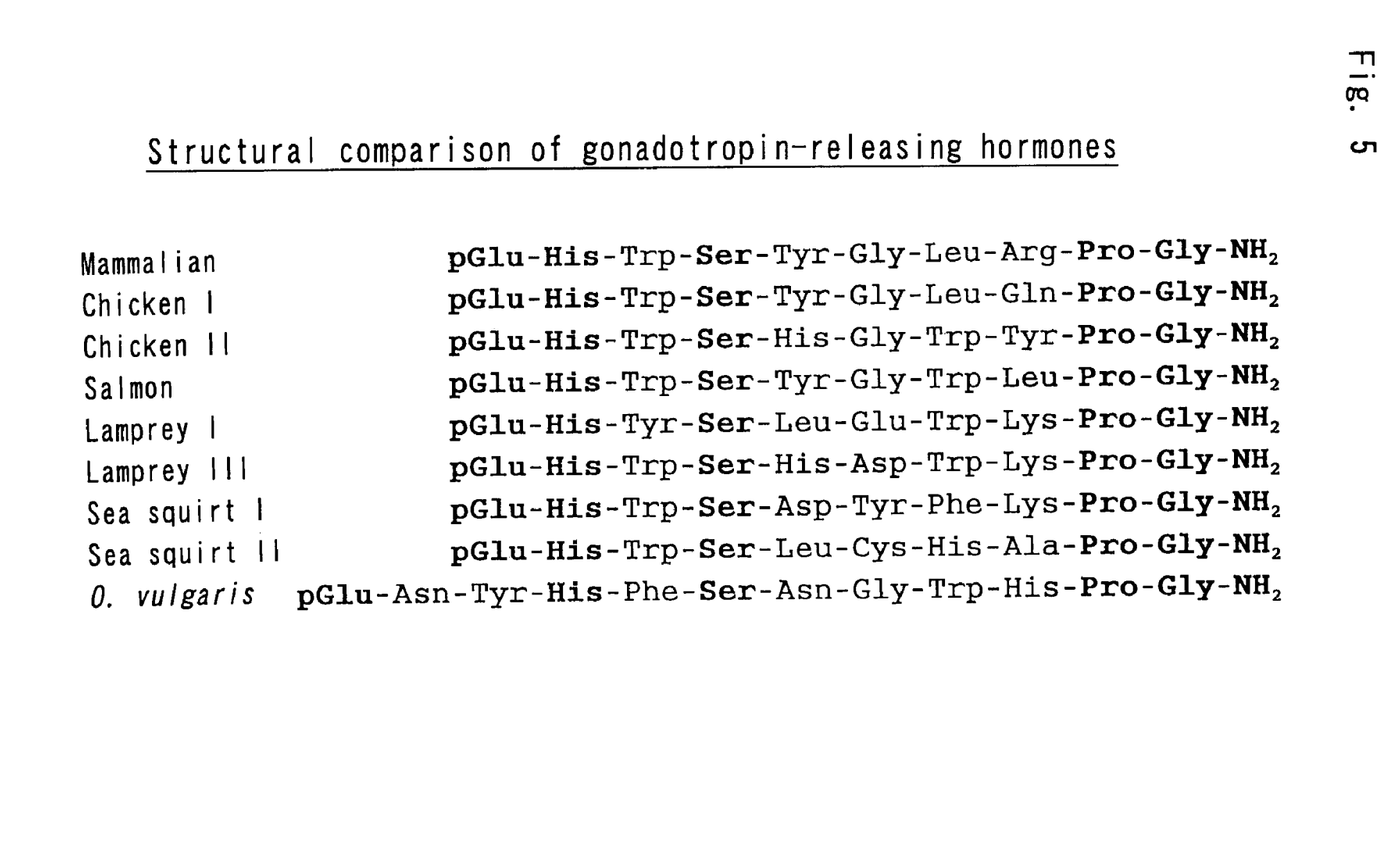
FIG. 5 is a comparative diagram showing structures of Compound (1), the peptide of the present invention, and of gonadotropin-releasing hormones identified in different vertebrates. The figure discloses SEQ ID NOS 19-26 and 1, respectively, in order of appearance.

As shown in FIG. 5, Compound (1) has a very high homology to the GnRHs identified in vertebrates. Unlike known decapeptide GnRHs, Compound (1) turned out to be a dodecapeptide.

The present inventors further conducted tests using quails and proved that Compound (1) has the activity of GnRH, namely, the activity to cause the release of luteinizing hormone (LH) from the pituitary gland of quails.

The present inventors also prepared a primer from the above amino acid sequence and performed a gene sequence analysis using the reverse transcriptase polymerase chain reaction (RT-PCR) on the total RNA obtained from the brains of *O. vulgaris*. In this manner, the present inventors determined that the precursor polypeptide of the peptide of the present invention has a total primary amino acid sequence shown as SEQ ID NO: 2.

The present inventors further determined that the gene encoding the precursor polypeptide has a base sequence shown as SEQ ID NO: 3, thereby completing the present invention.

Moreover, taking advantage of the decapeptide GnRH identified in vertebrates, the present inventors synthesized a new peptide similar to the peptide of the amino acid sequence (1) isolated from the brains of *O. vulgaris* by inserting two amino acid residues, Asn-Tyr, into the N-terminal region of the decapeptide GnRH between the first <Glu and the second His residues and examined its physiological activities.

Among other GnRHs, chicken-II-type GnRH (cGnRH-II) shown in FIG. 5 is commonly found in various classes of animals as well as in chickens. For this reason, the two amino acid residues, Asn-Tyr, were inserted into the N-terminal region of cGnRH-II between the first <Glu and the second His residues of the peptide to give a new peptide represented by the following amino acid sequence (2):

<Glu-Asn-Tyr-His-Trp-Ser-His-Gly-Trp-Tyr-Pro-Gly-NH₂ (SEQ ID NO: 5)    (2)

wherein <Glu represents pyroglutamic acid. The peptide may be referred to as Compound (2), hereinafter. Compound (2) was examined for the activity to enhance the heart beat of *O. vulgaris* and it was observed that Compound (2) showed an activity similar to Compound (1) isolated from the brains of *O. vulgaris* whereas cGnRH-II showed no such activity.

Furthermore, the present inventors deleted amino acids 2 and 3 from the N-terminal region of the dodecapeptide, which was isolated from invertebrates and had the GnRH activity, to convert it into a decapeptide similar to the GnRH isolated from vertebrates. As a result, it was observed that the decapeptide retained the initial GnRH activity.

To rephrase, the present inventors confirmed that the peptide represented by the following amino acid sequence (3), which is obtained by deletion of amino acids 2 and 3 from the N-terminal region of Compound (1) isolated from the brains of *O. vulgaris*, exhibits the GnRH activity:

<Glu-His-Phe-Ser-Asn-Gly-Trp-His-Pro-Gly-NH₂ (SEQ ID NO: 6)    (3)

wherein <Glu represents pyroglutamic acid. The peptide may be referred to as Compound (3), hereinafter.

Accordingly, the present invention provides a dodecapeptide having the activity of gonadotropin-releasing hormone (GnRH) and having the following amino acid sequence (I):

<Glu-Zaa-Zaa-His-Zaa-Ser-Zaa-Zaa-Zaa-Zaa-Pro-Gly-NH₂ (SEQ ID NO: 7)    (I)

wherein <Glu represents pyroglutamic acid and Zaa represents any amino acid.

The amino acid sequence (I) of the above-described peptide having the GnRH activity may be more specifically defined by the following amino acid sequence (II):

<Glu-Zaa-Zaa-His-Zaa-Ser-Zaa-Gly-Zaa-Zaa-Pro-Gly-NH₂ (SEQ ID NO: 8)    (II)

wherein <Glu represents pyroglutamic acid and Zaa represents any amino acid.

The amino acid sequence (I) of the above-described peptide having the GnRH activity may be even more specifically defined by the following amino acid sequence (III):

<Glu-Zaa-Zaa-His-Yaa-Ser-Zaa-Gly-Zaa-Zaa-Pro-Gly-NH₂ (SEQ ID NO: 9)    (III)

wherein <Glu represents pyroglutamic acid, Zaa represents any amino acid, and Yaa represents aromatic amino acid.

Of the peptides having the GnRH activity provided by the present invention, particularly preferred are those represented by the following amino acid sequences (1), (2) and (3):

<Glu-Asn-Tyr-His-Phe-Ser-Asn-Gly-Trp-His-Pro-Gly-NH₂ (SEQ ID NO: 1)    (1)

<Glu-Asn-Tyr-His-Trp-Ser-His-Gly-Trp-Tyr-Pro-Gly-NH₂ (SEQ ID NO: 5)    (2)

<Glu-His-Phe-Ser-Asn-Gly-Trp-His-Pro-Gly-NH₂ (SEQ ID NO: 6)    (3)

wherein <Glu represents pyroglutamic acid.

The present invention further provides a method for producing a pharmaceutical agent or a pesticide containing as an active ingredient the peptide of the amino acid sequence (I) having the GnRH activity, as well as a method for producing juvenile octopuses.

According to one aspect of the present invention, there is provided a precursor polypeptide having either an amino acid sequence of SEQ ID NO: 2, an amino acid sequence obtained by deletion or substitution of part of the amino acid of SEQ ID NO: 2, or an amino acid sequence obtained by addition of one or more amino acids to the amino acid sequence obtained by deletion or substitution of part of the amino acid of SEQ ID NO: 2.

According to another aspect of the present invention, there are provided a gene encoding the peptide and the precursor polypeptide of the present invention, in particular a gene having a base sequence of SEQ ID NO: 3, a vector incorporating these genes, and a host transformed by using the vector, and a method for producing, by means of genetic engineering, the peptide or the precursor polypeptide of the present invention by taking advantage of these genes.

BEST MODE FOR CARRYING OUT THE INVENTION

Novel peptides provided by the present invention act to cause the release of luteinizing hormone (LH) from the pituitary gland in quails and to enhance the heart beat in *Octopus vulgaris*. For this reason, the peptides can be isolated and purified from the brains of *O. vulgaris* on the basis of this activity toward the hearts of *O. vulgaris* as follows:

In one example, hot water extracts of brains of *O. vulgaris* are prepared. To the extract solution, acetic acid is added to a concentration of 3%. The solution is allowed to cool and is then centrifuged to obtain crude extracts. The extracts are adsorbed onto a C18 cartridge (e.g., Sep-Pak® Vac C18 cartridge manufactured by WATERS Co., Ltd.) and are then eluted with a 60% methanol containing 0.1% trifluoroacetic acid to collect a peptide fraction. The peptide fraction can be subjected to ion-exchange chromatography, reversed-phase chromatography, or other chromatography techniques to separate and purify peptides of interest.

Each being a dodecapeptide, the peptides of the present invention can be readily synthesized by solid-phase synthesis using a common peptide synthesizer (e.g., Peptide synthesizer 433A, manufactured by PE biosystems Japan Co., Ltd.) or any common techniques in synthetic organic chemistry. When necessary, the crude peptide products obtained by these techniques may be purified by common purification techniques such as reversed-phase high-performance liquid chromatography and crystallization.

The amino acid sequence of the precursor polypeptide of the peptide, as well as the base sequence encoding the precursor polypeptide in accordance with the present invention, may be determined in the following manner:

Using a primer synthesized based on the amino acid sequence of the present peptide obtained in the above-described manner, total RNA prepared from the brains of *O. vulgaris* is subjected to the reverse transcriptase polymerase chain reaction (RT-PCR) to determine the gene sequence of about 750 bp. Subsequently, the 5'-RACE and the 3'-RACE techniques are used to determine the gene sequence on the 5'-end and the 3'-end, respectively. According to the present invention, it was determined that the precursor polypeptide of the present peptide has an amino acid sequence shown as SEQ ID NO: 2 and the gene encoding the precursor polypeptide has a base sequence shown as SEQ ID NO: 3.

Accordingly, the precursor polypeptide of the peptide of the present invention, as well as the peptide of the present invention, can be produced using recombinant DNA techniques. When it is desired to produce the precursor polypeptide by using a recombinant DNA technique, a vector incorporating for example the gene of SEQ ID NO: 3 may be introduced into hosts for transformation. The hosts are subsequently cultured or grown, and the precursor polypeptide of interest is isolated and purified from the hosts or the culture solution of the hosts.

To obtain the peptide of interest from the precursor polypeptide, the precursor polypeptide may be processed and modified using an enzyme. If necessary, the peptide product may be subjected to an isolation or a purification process.

The peptides of the present invention each have an activity to enhance the heart beat of *O. vulgaris* and have a structure quite analogous to GnRH (peptide) of vertebrates. The peptides also act on the pituitary gland of quails to cause the release of luteinizing hormone. Furthermore, studies of the peptides of the present invention suggested that bird GnRH is related to the activity to enhance the heart beat in octopuses. These observations collectively indicate that the peptide in accordance with the present invention is in fact a hormone (peptide) involved in the release of gonadotropins in octopuses and other invertebrates, as well as in vertebrates.

Accordingly, the peptide of the present invention can serve as a useful material both for studying biology of octopuses including mechanisms of their reproduction and for studying structural correlations between GnRHs of invertebrates and those of vertebrates. Thus, the peptide will be of significant usefulness in the study of animal evolution. Also, the peptide of the present invention is expected to find use not only in the development of new substances with the activity of gonadotropin-releasing hormone, but also in the development of new medicines and pesticides using the peptide itself or peptide analogues thereof, as well as of new techniques for the production of juvenile octopuses.

For example, the peptide of the present invention may be used as an active ingredient in a medicine and may be formulated along with a pharmacologically acceptable excipient into proper oral or parenteral preparations, such as capsules, tablets, and injections. Specifically, the peptide of the present invention may be admixed with an excipient, such as lactose, starch or a derivative thereof, or a derivative of cellulose, and is encapsulated in gelatin capsules to form a capsule preparation.

When it is desired to form the peptide of the present invention into the form of tablets, a binder, such as carboxymethylcellulose sodium, alginic acid, and gum arabic, and water are added to the peptide in addition to the aforementioned excipient. The mixture is then kneaded and, if necessary, is formed into the form of granules. Subsequently, a lubricant, such as talc and magnesium stearate, is added to the mixture and the mixture is formed into tablets by a common compression tablet-making machine.

When it is desired to form the peptide of the present invention into preparations for parenteral administration, the peptide may be dissolved, along with a solubilizer, into sterilized distilled water or sterilized saline and is placed in sealed ampoules to provide a preparation for injection. When necessary, a stabilizer, a buffering agent, or other additives may be added to the preparation. Alternatively, the peptide of the present invention may be placed in vials in the form of powder so that, upon use, the powder can be dissolved in sterilized distilled water to form a solution preparation. These parenteral preparations may be delivered by intravenous administration or intravenous drip infusion.

Preferably, the dosage of the preparation containing the peptide of the present invention as an active ingredient is adjusted in consideration of various factors, including the disease to be treated, symptoms of the patient, severity of the symptom, age of the patient, and route of administration. In case of oral administration, the preparation is typically administered at a dose of 0.1 to 1,000 mg/day/human, preferably at a dose of 1 to 500 mg/day/human, whereas in case of parenteral administration, the preparation may be administered at a dose that is about 1/100 to about 1/2 the dose for oral administration.

Because of its nature as GnRH, the peptide of the present invention can be administered to cephalopods such as octopuses to cause the animals to reach sexual maturation at an earlier stage, so that the animals can be induced to start laying eggs at an earlier stage. Breeding and culturing these animals can facilitate production of juvenile cephalopods.

EXAMPLES

The present invention will now be described in detail in the following with reference to Examples, which are not intended to limit the scope of the invention in any way.

Example 1

Isolation of Cardioactive Peptides from *O. vulgaris*

(a) Crude Extraction

Brain tissue (including optic glands, optic tracts, and optic lobes) was taken from 100 specimens of *Octopus vulgaris* and was frozen in liquid nitrogen. The frozen tissue (180 g) was boiled in 900 ml distilled water for 10 min. After cooling, acetic acid was added to a concentration of 3% and the tissue was homogenized and then centrifuged at 4° C. at 12,000×g for 30 min to obtain a supernatant. To the resulting pellet, 200 ml of 3% acetic acid was added and the mixture was homogenized again for extraction. Subsequently, the mixture was centrifuged under the same conditions to obtain a supernatant. The supernatant was collected and concentrated in vacuo to a volume of about 200 ml to give crude extracts.

(b) Adsorption to C18 Cartridge

To the crude extracts obtained in the step (a) above, 5 ml of 6 M HCl was added and the mixture was centrifuged at 4° C. at 12,000×g for 30 min. The resulting supernatant was passed through Sep-Pak® Vac C18 cartridge (10 g, 35 cc, manufactured by WATERS Co., Ltd.) to allow the solutes to be adsorbed onto the cartridge. The cartridge was then washed with 200 ml of 0.1% trifluoroacetic acid (TFA, hereinafter), and the retained materials were then eluted with 100 ml of 60% methanol/0.1% TFA. The eluate was concentrated in vacuo and was freeze-dried to obtain 150 mg dried products.

(c) Reversed-phase High-performance Liquid Column Chromatography (1)

Using Capcell pak C18 UG80 (5 μm, 10 mm×250 mm, manufactured by SHISEIDO Co., Ltd.), the dried products obtained in the step (b) above were subjected to the reversed-phase high-performance liquid column chromatography (reversed-phase HPLC). Specifically, the dried products in 0.1% TFA (pH 2.2) were passed through the column at a flow rate of 1.5 ml/min and the retained materials were eluted with a linear gradient of acetonitrile in which the concentration of acetonitrile in TFA was linearly varied from 0% to 60% over 60 min. The eluate was collected in 3 ml fractions based on the UV-absorbance at 215 nm.

Each fraction was bioassayed according to the scheme described in Example 5 below and, as a result, it was found that a fraction eluted while the concentration of acetonitrile was varied from 26% to 30% had an activity to enhance the heart beat of *O. vulgaris*.

(d) Cation-exchange Column Chromatography

Using TSK gel SP-5PW (10 μm, 7.5 mm×75 mm, manufactured by TOSOH Co., Ltd.), the active fraction obtained in the step (c) above was subjected to the cation-exchange column chromatography (cation-exchange HPLC). Specifically, the fraction was loaded onto the column and was eluted with a 10 mM phosphate buffer (pH 7.0) at a flow rate of 1.0 ml/min while the concentration of NaCl in the phosphate buffer was linearly varied from 0 M to 0.6 M over 60 min (linear gradient). The eluate was collected in 2 ml fractions and each fraction was bioassayed. The activity was found in the fraction eluted when the concentration of NaCl was 0 M.

(e) Reversed-phase HPLC (2)

Using Capcell pak C18 UG80 (5 μm, 4.6 mm×150 mm, manufactured by SHISEIDO Co., Ltd.), the active fraction obtained in the step (d) above was subjected to the reversed-phase HPLC. Specifically, the fraction was loaded onto the column and was eluted with 0.1% TFA (pH 2.2) at a flow rate of 1.0 ml/min while the concentration of acetonitrile in TFA was linearly varied from 10 to 30% (linear gradient). The eluate was collected in 1 ml fractions. The activity was found in the fraction eluted when the concentration of acetonitrile was about 19.5%.

(f) Reversed-phase HPLC (3)

Figure 1:
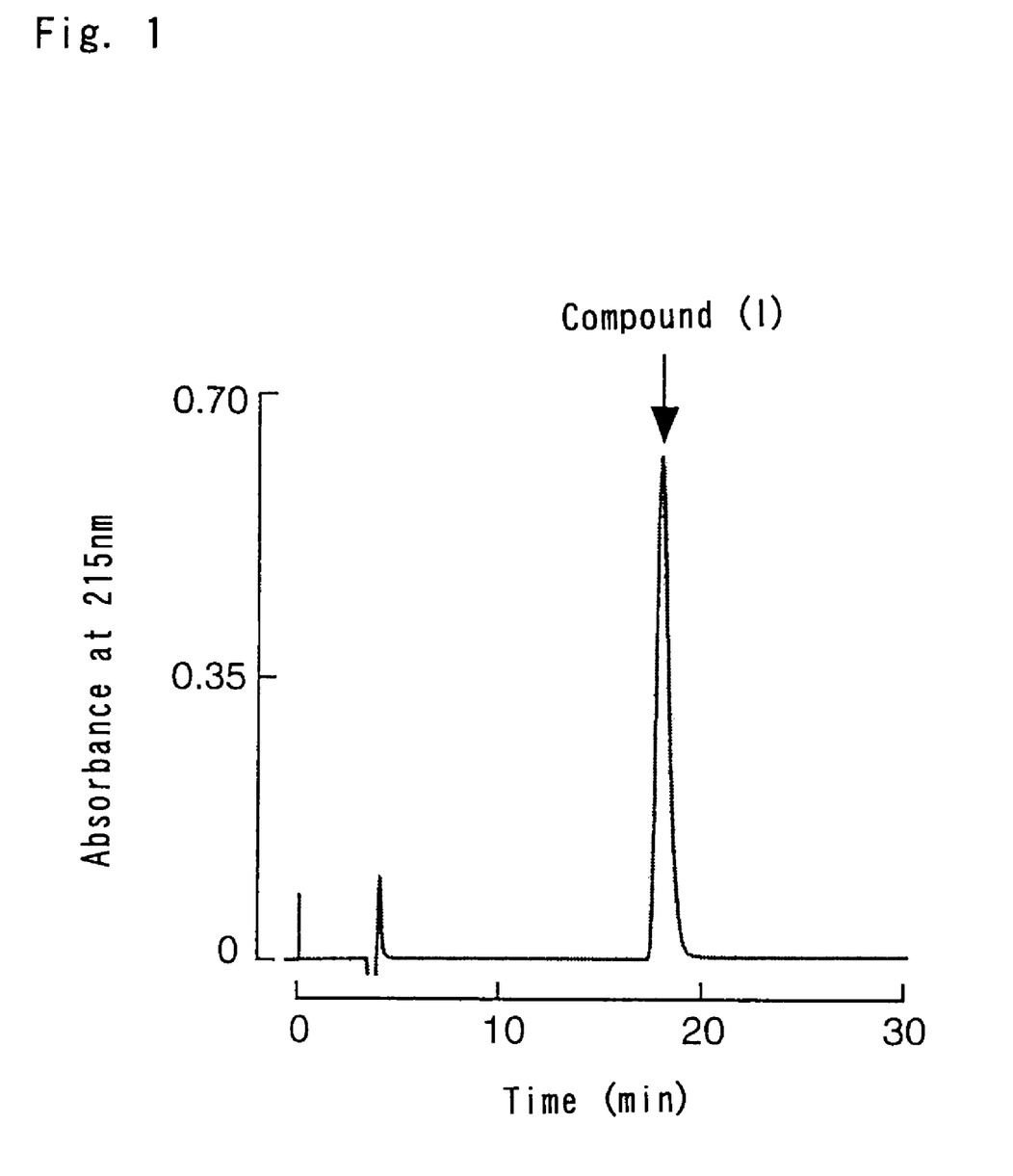
FIG. 1 is a diagram depicting the results of reversed-phase HPLC showing the final elution pattern of Compound (1), a peptide according to the present invention in Example 1.

Using Capcell pak C18 UG80 (5 μm, 4.6 mm×150 mm, manufactured by SHISEIDO Co., Ltd.), the active fraction obtained in the step (e) above was subjected to the reversed-phase HPLC. Specifically, the fraction was loaded onto the column and was eluted with 0.1% TFA (pH 2.2) having an acetonitrile concentration of 18% at a flow rate of 0.5 ml/min. A compound that exhibited a single peak was obtained at a retention time of 17.5 min. The compound was designated as Compound (1). A diagram showing the results of the reversed-phase HPLC was shown in FIG. 1.

Example 2

Structure Determination of Compound (1)

The structure analysis of Compound (1), purified in Example 1, by Shimadzu PSQ-1 protein sequencer (manufactured by SHIMADZU Co., Ltd.) could not determine the amino acid sequence of the peptide due to the modified N-terminal. Thus, the amino acid composition of the peptide was analyzed instead. The results are shown in Table 1 below.

TABLE 1

| Amino acid composition of the peptide | | |
|---|---|---|
| Amino acid | pmol | Molar ratio |
| Asx | 51.1 | 1.5 |
| Glx | 42.6 | 1.3 |
| Ser | 32.7 | 1.0 |
| Gly | 70.0 | 2.1 |
| His | 57.9 | 1.7 |
| Pro | 37.1 | 1.1 |
| Tyr | 24.2 | 0.7 |
| Phe | 33.8 | 1.0 |

The molecular weight of Compound (1) was determined by Q-TOF (Micromass, manufactured by UK Co.,Ltd.). The measurements are shown in Table 2 below.

TABLE 3

Mass spectrum data of the peptide

| Compound | Molecular formula | Calculated value $(M + 2H)^{2+}$ | Calculated value $(M + 2H)^{2+}$ |
|---|---|---|---|
| Before treatment with enzyme | $C_{66}H_{80}N_{20}O_{17}$ | 713.30 | 713.30 |
| After treatment with enzyme | $C_{61}H_{75}N_{19}O_{15}$ | 657.79 | 657.85 |

It was determined from the analysis of the amino acid composition and the measurement of the molecular weight that the N-terminal of Compound (1) includes a pyroglutamic acid residue. Accordingly, Compound (1) was treated with an enzyme capable of cleaving off the first pyroglutamic acid residue (pyroglutamate aminopeptidase, manufactured by TAKARA SHUZO Co., Ltd.) and was again analyzed by the protein sequencer.

Consequently, the amino acid sequence of Compound (1) was determined, starting from the second amino acid residue, and the presence of Trp, which cannot be detected by the composition analysis, was verified.

The amino acid sequence determined is shown in Table 3 below.

TABLE 3

Amino acid sequence of the peptide after treatment with enzyme (pmol)

| Cycle | Amino acid | |
|---|---|---|
| 1 | Asn | 27 |
| 2 | Tyr | 25 |
| 3 | His | 7 |
| 4 | Phe | 23 |
| 5 | Ser | 3 |
| 6 | Asn | 16 |
| 7 | Gly | 12 |
| 8 | Trp | 3 |
| 9 | His | 2 |
| 10 | Pro | 5 |
| 11 | Gly | 4 |

To make sure that the enzyme treatment had worked as intended, the molecular weight of Compound (1) after the treatment was again determined by Q-TOF (Micromass, manufactured by UK Co., Ltd.) in the same manner and, as a result, it was verified that the first pyroglutamic acid residue had been cleaved off. The results are also shown in Table 2 above.

Through the foregoing instrumental analyses, it was determined that Compound (1), a neuropeptide isolated and purified from *O. vulgaris*, has the following amino acid sequence (1):

<Glu-Asn-Tyr-His-Phe-Ser-Asn-Gly-Trp-His-Pro-Gly-NH₂ (SEQ ID NO: 1)    (1)

wherein <Glu represents pyroglutamic acid.

Example 3

Synthesis of Compound (1) by the Solid Phase Method

Using a fully automated peptide synthesizer 433A (PE Biosystems Japan), Compound (1) was synthesized according to FastMoc® chemistry.

In the synthesis, an Fmoc-NH-SAL-A resin (manufactured by WATANABE CHEMICAL INDUSTRIES, Ltd.) to serve as a solid support was used, along with pyroglutamic acid, Fmoc-Asn-(Trt), Fmoc-Tyr-(tBu), Fmoc-His-(Trt), Fmoc-Phe, Fmoc-Ser-(tBu), Fmoc-Gly, Fmoc-Trp-(tBoc), and Fmoc-Pro.

As used herein, Fmoc represents 9-fluorenylmethoxycarbonyl, tBu represents t-butyl, Trt represents trityl, and tBoc represents t-butyloxycarbonyl.

A 10 ml mixture of 2.5% 1,2-ethanedithiol/2.5% water/95% TFA containing 100 mg 2-methylindole was used for the purposes of cleavage of the crude peptide from the peptide resin upon completion of the reaction and deprotection of the crude peptide. After the reaction, the reaction mixture was filtered. Ether was then added to the filtrates to cause the peptide to precipitate. The precipitates were washed three times with ether to obtain about 100 mg of crude peptide, about 10 mg of which was then purified by the reversed-phased HPLC to obtain about 6 mg of purified peptide.

When subjected to the reversed-phase HPLC using Capcell pak C18, the purified peptide eluted exactly at the same retention time as Compound (1). Also, the synthetic peptide exhibited the same cardioactivity toward the heart beat of *O. vulgaris* as did the naturally-occurring peptide.

Example 4

Synthesis of Compounds (2) and (3) by the Solid Phase Method

Peptides represented by the following amino acid sequences (2) and (3) were synthesized in the same manner as in Example 3 above:

<Glu-Asn-Tyr-His-Trp-Ser-His-Gly-Trp-Tyr-Pro-Gly-NH² (SEQ ID NO: 5)    (2)

<Glu-His-Phe-Ser-Asn-Gly-Trp-His-Pro-Gly-NH₂ (SEQ ID NO: 6)    (3)

wherein <Glu represents pyroglutamic acid.

Example 5

Measurement of the Heart Beat Activity of *O. vulgaris*

The heart beat activity of *O. vulgaris* was measured according to the method proposed by Morishita et al (Fumihiro Morishita, *Biochem. Biophys. Res. Commun.*, 240, 354-358 (1997)). Specifically, the heart was taken from *O. vulgaris* and the atria were removed from the heart. A cannula was inserted from each atrium into the ventricle and was at the same time connected to a chamber (80 ml in volume) by tying with a cotton thread. The aorta was pinched to prevent leakage of liquid from the ventricle and was connected to a tension transducer. This completed preparation of the heart to serve as a specimen for the assay. Each cannula was adjusted to permit a 1 to 2 ml/min flow of artificial sea water (containing 0.1% glucose). Each of the analytes to be assayed was dissolved in 1 ml of the same artificial sea-water, and the resulting solution was injected into the heart through the cannulae. The variation of the heart beat was recorded.

As test compounds, Compound (1) isolated from the brains of *O. vulgaris*, Compound (2), and cGnRH-II, a vertebrate GnRH isolated from chickens and used to derive Compound (2) therefrom, were used.

Figure 2:
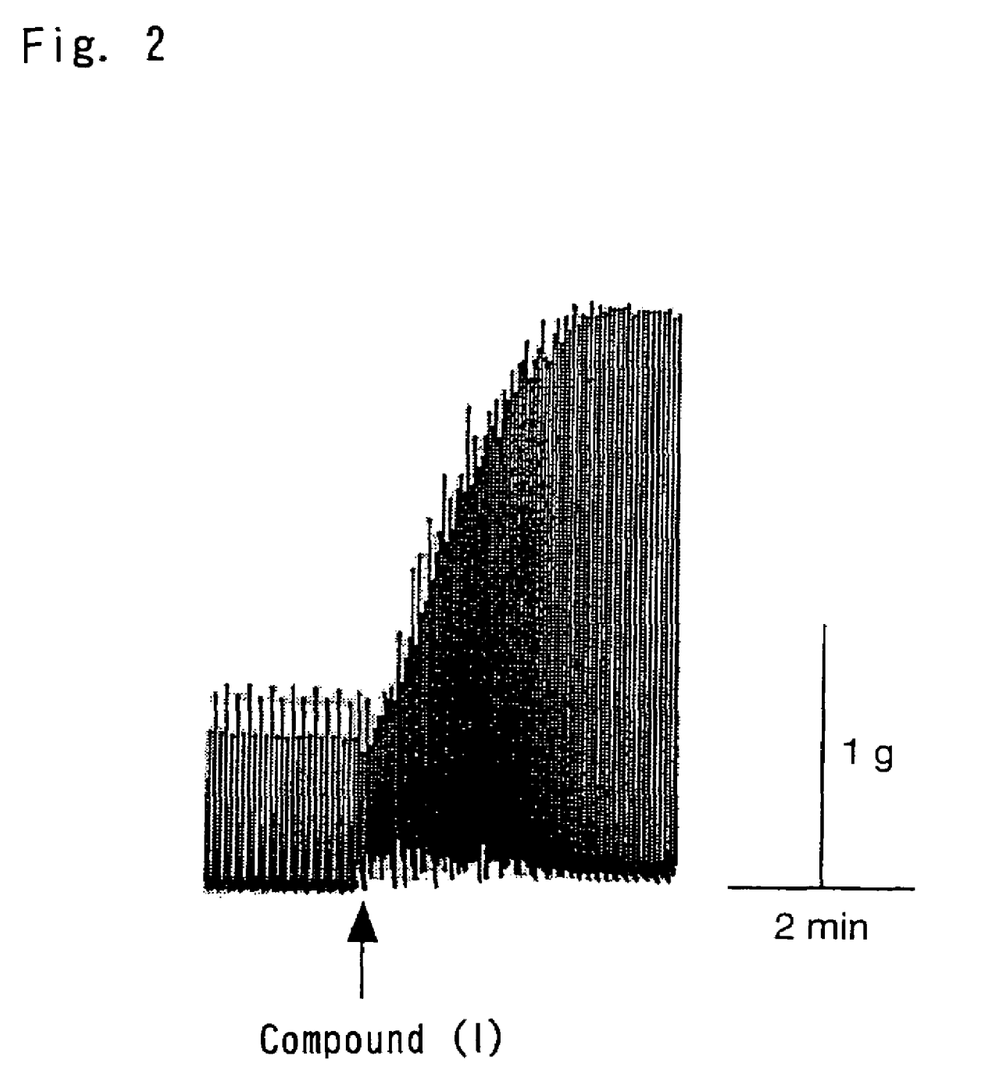
FIG. 2 is a diagram showing the heart beat of *O. vulgaris* when an amount of Compound (1), the peptide of the present invention, corresponding to one specimen of *O. vulgaris* was added to a chamber in Example 5.

As shown in FIG. 2, the results indicate that Compound (1) enhanced the heart beat of *O. vulgaris*.

Figure 3:
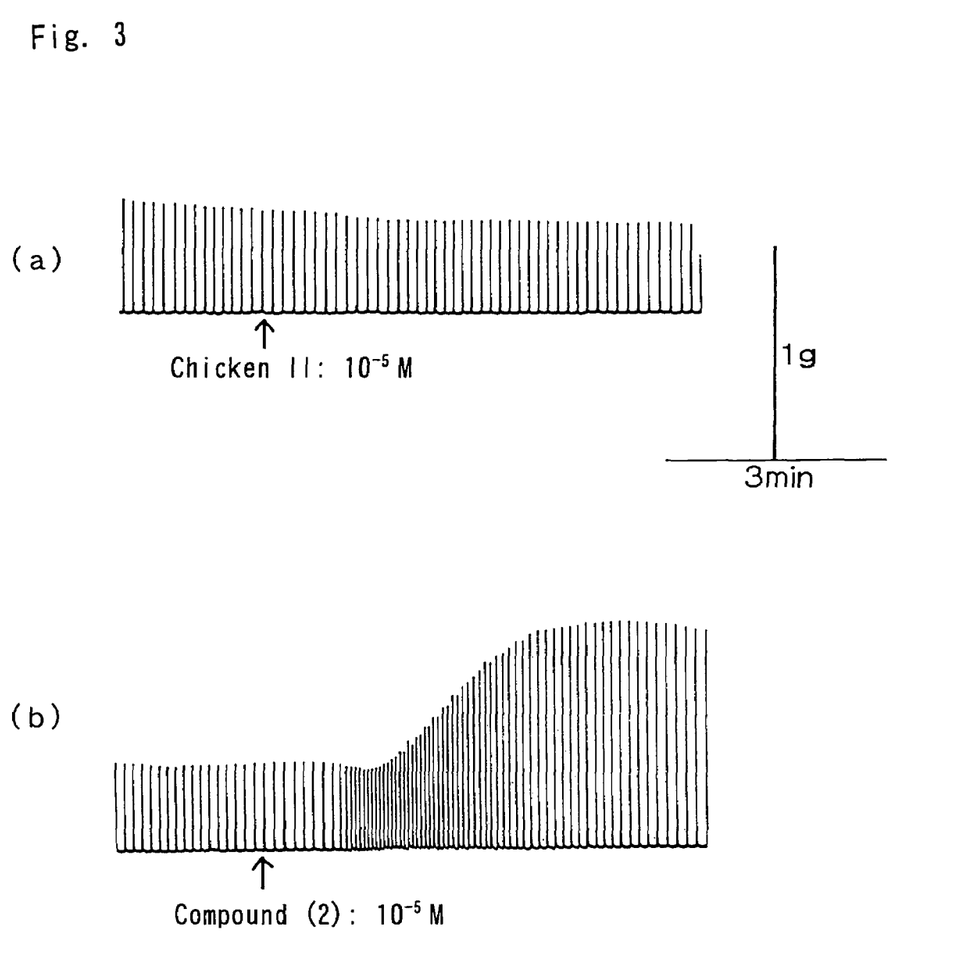
FIG. 3 includes diagrams showing the results of Example 5, wherein the diagrams show variation in the heart beat of *O. vulgaris* (a) when $10^{-5}$ M cGnRH-II was added to the chamber and (b) when $10^{-5}$ M Compound (2), the peptide of the present invention, was added to the chamber, respectively.

As shown in FIG. 3(*b*), Compound (2) also enhanced the heart beat of *O. vulgaris* by increasing both the heart rate and the amplitude of the heart beat. In contrast, cGnRH-II, as can be seen from FIG. 3(*a*), did not have any effect on the heart rate or the amplitude of the heart beat of *O. vulgaris*.

Example 6

Effects on the Pituitary Glands of Quails

Cells taken from the pituitary glands of quails were inoculated onto a 24-well plate at $7.5 \times 10^5$ cells/well (substantially equivalent to two animals). The cells were then incubated for 3 days in a culture medium containing fetal calf serum. The cells were incubated for another 24 hrs in 1 ml serum-free medium. After the incubation period, the peptide solution was added to the culture medium to final concentrations of 0, $10^{-9}$, $10^{-8}$, $10^{-7}$, $10^{-6}$, and $10^{-5}$ M, respectively, and the cultures were further incubated for 4 hrs. The supernatant was then collected from each culture. For each concentration, 5 samples were subjected to radioimmunoassay and measurements were taken. The data were statistically analyzed by one-way analysis of variance (ANOVA).

Figure 4:
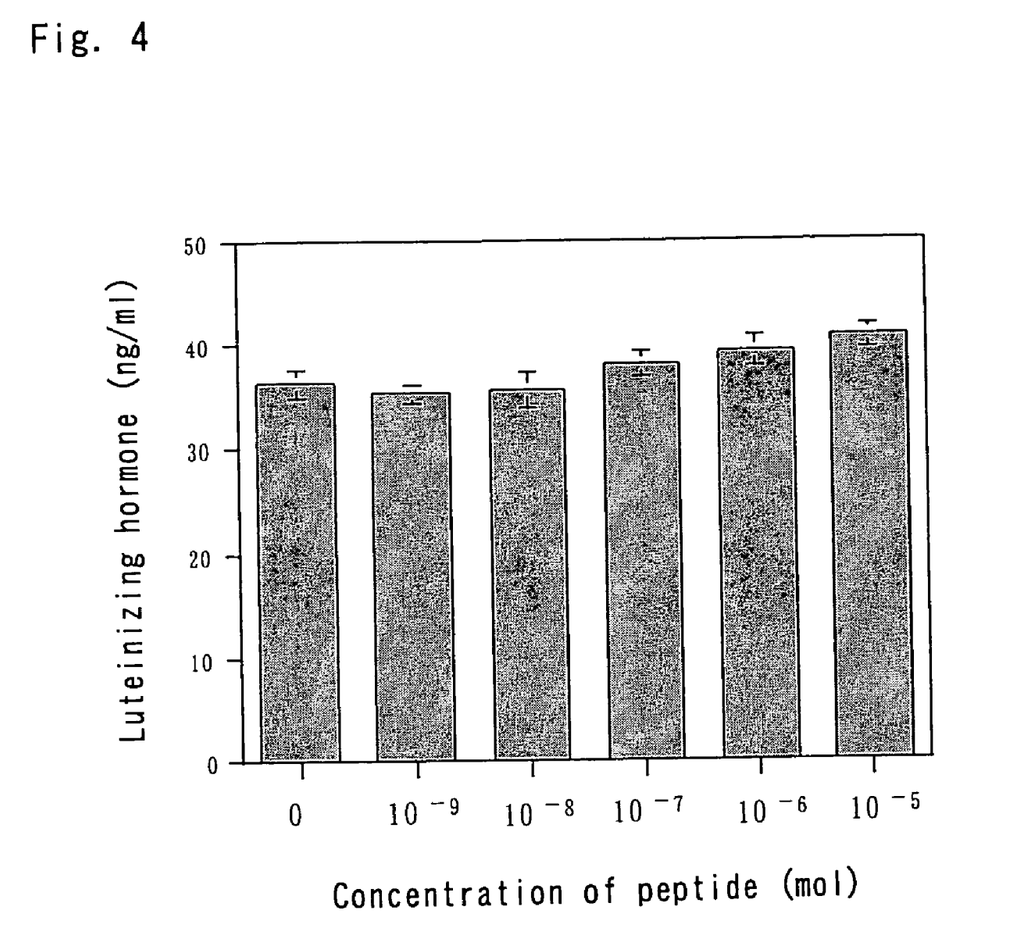
FIG. 4 is a graph showing the amounts of released luteinizing hormone (LH) when Compound (1), the peptide of the present invention, was applied to the pituitary gland of a quail in Example 6.

The results are shown in FIG. 4. As shown, the statistical analysis revealed that Compound (1), the peptide of the present invention, significantly increased the release of luteinizing hormone (LH).

When tested in the same manner, Compound (3) also proved to increase the release of luteinizing hormone (LH).

Example 7

Determination of the Entire Amino Acid Structure of the Precursor Polypeptide and Determination of the Base Sequence of the Gene Encoding the Polypeptide (1) Preparation of Total RNA of the Brain of *O. vulgaris*

About 1 g of the brain of *O. vulgaris* was crushed in liquid nitrogen, dissolved in 10 ml TRIzol® reagent (GIBCO BRL Co., Ltd.), and homogenized. At room temperature, the homogenates were allowed to stand for 5 min and were divided into 1 ml aliquots. To each aliquot, 200 µl chloroform was added and the mixture was stirred. The mixture was then centrifuged (15,000 rpm, 15 min, 4° C.) in a cold centrifuge (SAKUMA SEISAKUSHO Co., Ltd.). Following the centrifugation, the top aqueous layer was removed and 0.5 ml isopropanol was added to the aqueous phase. The mixture was then allowed to stand for 10 min at room temperature and was further centrifuged (15,000 rpm, 10 min, 4° C.) in the cold centrifuge. The supernatant was removed and the pellet was resuspended in 1 ml 75% ethanol. The suspension was centrifuged again (10,000 rpm, 5 min, 4° C.). Subsequently, the supernatant was removed and the pellet was air-dried for about 10 min. The RNA pellet was then dissolved in 10 µl DPEC-treated water by incubating at 60° C. for 10 min. In this manner, about 3 mg of total RNA was obtained.

(2) Degenerate 3'-RACE

The following degenerate primers were designed based on the amino acid sequence of the peptide isolated from the brain of *O. vulgaris* and synthesized by an ordinary method:

Primer-1: 5'-CA(A/G)AA(C/T)TA(C/T)CA(C/T)TT (C/T)IIIAA(C/T)GG-3' (SEQ ID NO: 10)

Primer-2: 5'-(T/A)(C/G)IAA(C/T)GGITGGCA(C/T) CCIGG-3' (SEQ ID NO: 11)

wherein each letter is based on the definition in "Table of Nucleotide Codes"(Biology experiment illustrated, supplement to Cell Engineering, SHUJUNSHA Co., Ltd., The same codes are used, hereinafter).

Using a 5'/3'-RACE Kit (Boehringer Mannheim Co., Ltd.), degenerate 3'-RACE was performed according to the following protocol: 2 µg total RNA, 4 µl cDNA synthesis buffer, 2 µl dNTP mix, 1 µl oligo dT-anchor primer (12.5 pmol/µl), 1 µl AMV reverse transcriptase (20 units/µl), and DEPC-treated water were added to one another to give a total volume of 20 µl. The mixture was incubated at 55° C. for 60 min and then at 65° C. for 10 min to synthesize 1st-strand cDNA.

Next, 1st-3'-RACE was performed according to the following procedure: 3 µl 1st-strand cDNA, 5 µl 10×PCR buffer, 8 µl dNTP mix, 5 µl Primer-1 (100 pmol/µl), 1 µl PCR anchor primer (12.5 pmol/µl), 0.5 µl TaKaRa Ex Taq® (TAKARA SHUZO Co., Ltd), and water were mixed with each other to give a total volume of 50 µl. The mixture was incubated at 94° C. for 5 min, followed by 30 cycles of 94° C. for 30 sec, 49° C. for 30 sec, and 72° C. for 2 min, which was followed by incubation at 72° C. for 5 min. GeneAmp PCR System 2400 thermal cycler (Perkin Elmer Co., Ltd.) was used to carry out the PCR.

Subsequently, the 1st-PCR products were purified through a spin column (MicroSpin® S-400, manufactured by Amersham Pharmacia Co., Ltd.) and were subjected to 2nd-3'-RACE according to the following procedure: 5 µl 1st-PCR products, 5 µl 10×PCR buffer, 8 µl dNTP mix, 5 µl Primer-2 (100 pmol/µl), 1 µl PCR anchor primer (12.5 pmol/µl), 0.5 µl TaKaRa Ex Taq® (TAKARA SHUZO Co., Ltd), and water were mixed with each other to give a total volume of 50 µl. The mixture was incubated at 94° C. for 5 min, followed by 30 cycles of 94° C. for 30 sec, 51° C. for 30 sec, and 72° C. for 1 min, which was followed by incubation at 72° C. for 7 min.

Five microliter of the reaction mixture was then electrophoresed on a 1.5% agarose gel. Bands were observed at about 400 bp and about 600 bp, indicating amplification of two PCR products.

(3) Collection of PCR Products

Five microliter of the PCR products was electrophoresed on a 1.5% agarose gel and the two PCR product bands formed at about 400 bp and about 600 bp were cut out. Using Gel Extraction Kit (QIAGEN Co., Ltd.), DNA was collected from the gel. To confirm the results, 3 µl of each of the collected DNA fragments was electrophoresed on a 1.5% agarose gel. As a result, the two PCR products were observed at about 400 bp and about 600 bp, respectively.

(4) Ligation of the PCR Products

The two PCR products, sized about 400 bp and about 600 bp, respectively, were individually purified through a spin column. For each of the PCR products, 3 µl of PCR product, 2 µl TA cloning vector pCR2.1 (Invitrogene Co., Ltd.), and 5 µl Ligation High (TOYOBO Co., Ltd.) were mixed with each other, and the mixture was allowed to react for 1 hr at 16° C. (ligation).

(5) Transformation of *E. coli*

Each of the two 10 µl ligation mixtures obtained in the step (4) above was mixed with highly competent *E. coli*

DH5α (TOYOBO Co., Ltd.). The mixture was placed in an ice bath for 30 min and was then subjected to heat-shock at 42° C. for 50 sec, followed by chilling on ice for 2 min. After chilling, 1 ml SOC medium was added and the mixture was incubated at 37° C. for 10 min. Subsequently, 35 µl X-gal was evenly spread onto the surface of LB/Amp agar medium (LB containing 50 µg/ml ampicilin), and 50 µl transformant was inoculated onto the medium. The remaining transformant was centrifuged at 10,000 rpm for 1 min to a volume of about 100 µl and the whole transformant was also inoculated onto the LB/Amp agar medium. The culture medium was incubated overnight at 37° C.

(6) Colony PCR

Using the colonies obtained above as a template, the colony PCR was performed. Specifically, the *E. coli* cells, 5 µl 10× reaction buffer, 5 µl 2 mM dNTPs, 3 µl 25 MM MgCl$_2$, 0.5 µl M13FW primer (100 pmol/µl), 0.5 µl M13RV primer (100 pmol/µl), 0.5 µl rtaq DNA polymerase (TOYOBO Co., Ltd.), and water were mixed with each other to give a total volume of 50 µl. The mixture was incubated at 90° C. for 10 min, followed by 30 cycles of 94° C. for 30 sec, 55° C. for 30 sec, and 72° C. for 1 min. Three microliter of the reaction mixture was electrophoresed on a 1.5% agarose gel.

The M13FW and M13RV primers, the base sequences of which are shown below, were synthesized by an ordinary method:

M13FW: 5'-GTAAAACGACGGCCAGTG-3' (SEQ ID NO: 12)

M13RV: 5'-GGAAACAGCTATGACCATG-3'. (SEQ ID NO: 13)

(7) DNA Sequence

The colony PCR products of the size of interest (about 600 bp and about 800 bp) were purified through a spin column and were sequenced by DNA Sequencing Kit (PE Biosystems, Co., Ltd.). ABI PRISM 310 Genetic Analyzer (PE Biosystems, Co., Ltd.) was used for sequencing.

Through the sequence analysis by a gene-analyzing software GENETYX-MAC (SOFTWARE KAIHATSU Co., Ltd.), the cDNA sequence of the about 800 bp fragment was determined. A further DNA sequencing revealed that the cDNA sequence of the fragment of about 600 bp was in fact part of the cDNA sequence of the fragment of about 800 bp.

(8) 5'-RACE

The following primers were synthesized according to the base sequences of the cDNA fragments.

5'-RACE-1: 5'-GGTCTGCAATCTCATTGACC-3' (SEQ ID NO: 14)

5'-RACE-2: 5'-TGCCAGTCAGGATTTCTCTC-3' (SEQ ID NO: 15)

5'-RACE-3: 5'-TCTTGGTGTTTGTCGGAAGG-3' (SEQ ID NO: 16)

Using 5'/3'-RACE Kit (Boehringer Mannheim Co., Ltd.), 5'-RACE was performed according to the following protocol: 2 µg total RNA, 1 µl 5'-RACE-1 (12.5 pmol/µl), 4 µl cDNA synthesis buffer, 2 µl dNTP mix, 1 µl AMV reverse transcriptase (20 units/µl), and DEPC-treated water were mixed with each other to give a total volume of 20 µl. The mixture was incubated at 55° C. for 60 min and then at 65° C. for another 10 min to synthesize 1st-strand cDNA.

After purification through a spin column, the 1st-strand cDNA was mixed with 2.5 µl reaction buffer and 2.5 µl 2 mM dNTP, and the mixture was incubated at 94° C. for 3 min, followed by chilling on ice. Subsequently, 1 µl terminal transferase (10 units/µl) was added to the mixture, and the mixture was incubated at 37° C. for 20 min and then at 70° C. for another 10 min to synthesize da-tailed cDNA.

Next, 1st-PCR and 2nd-PCR were conducted under the following conditions:

(a) 1st-PCR

Three microliter dA-tailed cDNA, 5 µl 10×PCR buffer, 8 µl dNTP mix, 1 µl 5'-RACE-2 (12.5 pmol/µl), 1 µl oligo dT-anchor primer (12.5 pmol/µl), 0.5 µl TaKaRa Ex Taq® (TAKARA SHUZO Co., Ltd) and water were mixed with each other to give a total volume of 50 µl. The mixture was incubated at 94° C. for 5 min, followed by 30 cycles of 94° C. for 30 sec, 55° C. for 30 sec, and 72° C. for 3 min, which was followed by incubation at 72° C. for 5 min.

(b) 2nd-PCR

Five microliter of the 1st-PCR product purified through a spin column, 5 µl 10×PCR buffer, 8 µl DNTP mix, 1 µl 5'-RACE-3 (12.5 pmol/µl), 1 µl PCR-anchor primer (12.5 pmol/l), 0.5 µl TaKaRa Ex Taq® (TAKARA SHUZO Co., Ltd) and water were mixed with each other to give a total volume of 50 µl. PCR was then carried out by using the same cycle conditions as in the 1st-PCR.

The resulting 2nd-PCR product was electrophoresed on a 1.5% agarose gel. As a result, a band was observed at about 600 bp.

The base sequence of the 2nd-PCR product was determined according to the protocol described in (4), (5), (6), and (7) above.

Through the foregoing analyses, the size of cDNA (about 700 bp) and the base sequence were determined for the gene encoding the precursor polypeptide of the peptide of the present invention. Also, the estimated number of amino acids (89 amino acid residues), as well as the amino acid sequence, was determined for the precursor polypeptide of the peptide of the present invention.

Figure 6:
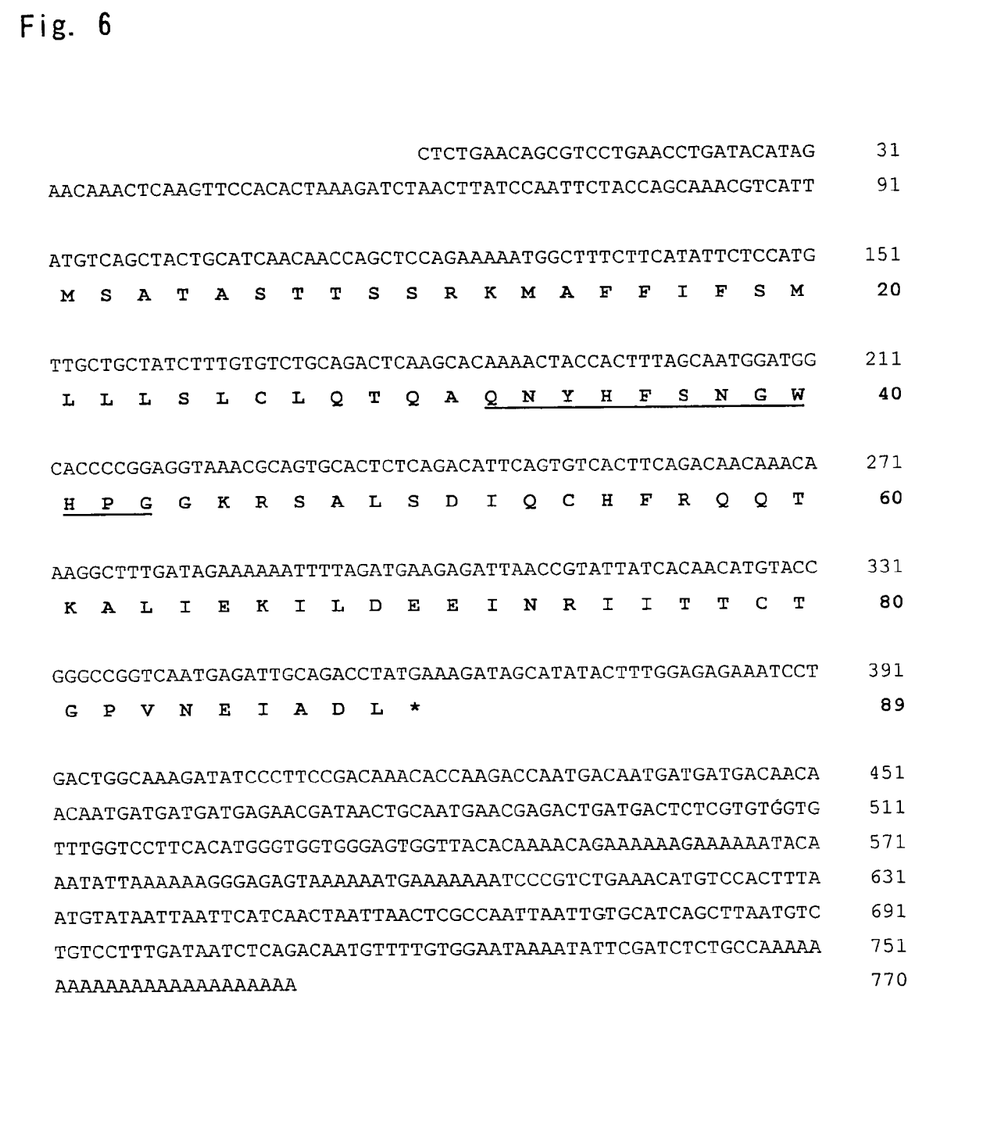
FIG. 6 shows the amino acid sequence of the precursor polypeptide of the present invention, in which the part corresponding to the peptide of the present invention is underlined. The disclosed nucleotide sequence is SEQ ID NO: 3.

The amino acid sequence of the precursor polypeptide and the base sequence of the gene (cDNA) encoding the precursor polypeptide are shown as SEQ ID NO: 2 and SEQ ID NO: 3, respectively. Also, the part of the amino acid sequence of the precursor polypeptide that corresponds to the peptide of the present invention is shown in FIG. 6.

In the figure, the part corresponding to the amino acid sequence of the peptide of the present invention is underlined.

Example 8

Exemplary Preparation

| Tablets Composition: | |
| --- | --- |
| Compound (1) | 10 g |
| lactose | 125 g |
| microcrystalline cellulose | 25 g |
| corn starch | 25 g |
| 5% hydroxypropyl methylcellulose | 100 ml |
| magnesium stearate | 5 g |

According to a known method, the above components were kneaded, granulated, dried and shaped into tablets to obtain tablets, each weighing 190 mg and containing 10 mg of Compound (1) as an active ingredient.

INDUSTRIAL APPLICABILITY

As shown in FIG. 5, the peptide of the present invention, which acts to enhance the heart beat of *O. vulgaris*, has a structure highly analogous to gonadotropin-releasing hormone (peptide) of vertebrates. Together with this finding, the fact that the peptide acts on the pituitary gland of quails to cause the release of luteinizing hormone implies that the peptide is in fact a hormone (peptide) involved in the release of gonadotropin in octopuses.

Thus, studying the activities of the present peptide will help understand biology of octopuses including their breeding mechanisms as well as processes of animal evolution.

Not only does the peptide of the present invention serve as a useful tool in developing new substances with the activity of gonadotropin-releasing hormone, but it also may lead to development of new medicines and pesticides that make use of the peptide itself or peptide analogues, as well as of new techniques for the production of juvenile octopuses.

The invention claimed is:

1. An isolated peptide having the activity of gonadotropin-releasing hormone (GnRH) and having the following amino acid sequence (I):

<Glu-Zaa-Zaa-His-Zaa-Ser-Zaa-Zaa-Zaa-Pro-Gly-NH$_2$ (SEQ ID NO: 7)     (I)

wherein <Glu represents pyroglutamic acid and Zaa represents any amino acid.

2. The peptide having the GnRH activity according to claim 1, having the following amino acid sequence (II):

<Glu-Zaa-Zaa-His-Zaa-Ser-Zaa-Gly-Zaa-Zaa-Pro-Gly-NH$_2$ (SEQ ID NO: 8)     (II)

wherein <Glu represents pyroglutamic acid and Zaa represents any amino acid.

3. The peptide having the GnRH activity according to claim 2, having the following amino acid sequence (III):

<Glu-Zaa-Zaa-His-Yaa-Ser-Zaa-Gly-Zaa-Zaa-Pro-Gly-NH$_2$ (SEQ ID NO: 9)     (III)

wherein <Glu represents pyroglutamic acid, Zaa represents any amino acid, and Yaa represents aromatic amino acid.

4. The peptide according to claim 3 having the following amino acid sequence (1):

<Glu-Asn-Tyr-His-Phe-Ser-Asn-Gly-Trp-His-Pro-Gly-NH$_2$ (SEQ ID NO: 1)     (1)

wherein <Glu represents pyroglutamic acid.

5. The peptide according to any one of claims 1-3, and 4 obtained from brains of *Octopus vulgaris*.

6. The peptide according to any one of claims 1 to 3 having an amino acid sequence obtained by inserting two amino acid residues, Asn-Tyr, into the N-terminal region of a vertebrate GnRH between amino acids 1 (<Glu) and 2 (His).

7. The peptide according to claim 6 having the following amino acid sequence (2):

<Glu-Asn-Tyr-His-Trp-Ser-His-Gly-Trp-Tyr-Pro-Gly-NH$_2$ (SEQ ID NO: 5)     (2)

wherein <Glu represents pyroglutamic acid.

8. A pharmaceutical agent or a pesticide containing as an active ingredient the peptide having the activity of gonadotropin-releasing hormone (GnRH) of any one of claims 1-3, and 4.

9. A method for producing juvenile cephalopods making use of the peptide having the activity of gonadotropin-releasing hormone (GnRH) of any one of claims 1-3, and 4.

* * * * *

SEQUENCE LISTING

```
<160> NUMBER OF SEQ ID NOS: 4

<210> SEQ ID NO 1
<211> LENGTH: 12
<212> TYPE: PRT
<213> ORGANISM: Octopus vulgaris
<220> FEATURE:
<221> NAME/KEY: MISC_FEATURE
<222> LOCATION: (1)..(1)
<223> OTHER INFORMATION: Xaa is pyroglutamic acid residue, Glu.
      C terminal is amidated.

<400> SEQUENCE: 1

Xaa Asn Tyr His Phe Ser Asn Gly Trp His Pro Gly
1               5                   10

<210> SEQ ID NO 2
<211> LENGTH: 89
<212> TYPE: PRT
<213> ORGANISM: Octopus vulgaris

<400> SEQUENCE: 2

Met Ser Ala Thr Ala Ser Thr Thr Ser Ser Arg Lys Met Ala Phe Phe
1               5                   10                  15

Ile Phe Ser Met Leu Leu Leu Ser Leu Cys Leu Gln Thr Gln Ala Gln
            20                  25                  30

Asn Tyr His Phe Ser Asn Gly Trp His Pro Gly Gly Lys Arg Ser Ala
        35                  40                  45

Leu Ser Asp Ile Gln Cys His Phe Arg Gln Gln Thr Lys Ala Leu Ile
    50                  55                  60

Glu Lys Ile Leu Asp Glu Glu Ile Asn Arg Ile Ile Thr Thr Cys Thr
65                  70                  75                  80

Gly Pro Val Asn Glu Ile Ala Asp Leu
                85

<210> SEQ ID NO 3
<211> LENGTH: 770
<212> TYPE: DNA
<213> ORGANISM: Octopus vulgaris
<220> FEATURE:
<221> NAME/KEY: CDS
<222> LOCATION: (92)..(358)
<223> OTHER INFORMATION:

<400> SEQUENCE: 3
ctctgaacag cgtcctgaac ctgatacata gaacaaactc aagttccaca ctaaagatct      60
aacttatcca attctaccag caaacgtcat t atg tca gct act gca tca aca       112
                                  Met Ser Ala Thr Ala Ser Thr
                                  1               5 acc agc tcc aga aaa atg gct ttc ttc ata ttc tcc atg ttg ctg cta      160
```

-continued

```
      Thr Ser Ser Arg Lys Met Ala Phe Phe Ile Phe Ser Met Leu Leu Leu
              10                  15                  20 tct ttg tgt ctg cag act caa gca caa aac tac cac ttt agc aat gga          208
Ser Leu Cys Leu Gln Thr Gln Ala Gln Asn Tyr His Phe Ser Asn Gly
    25                  30                  35 tgg cac ccc gga ggt aaa cgc agt gca ctc tca gac att cag tgt cac          256
Trp His Pro Gly Gly Lys Arg Ser Ala Leu Ser Asp Ile Gln Cys His
40                  45                  50                  55 ttc aga caa caa aca aag gct ttg ata gaa aaa att tta gat gaa gag          304
Phe Arg Gln Gln Thr Lys Ala Leu Ile Glu Lys Ile Leu Asp Glu Glu
                60                  65                  70 att aac cgt att atc aca aca tgt acc ggg ccg gtc aat gag att gca          352
Ile Asn Arg Ile Ile Thr Thr Cys Thr Gly Pro Val Asn Glu Ile Ala
                75                  80                  85 gac cta tgaaagatag catatacttt ggagagaaat cctgactggc aaagatatcc           408
Asp Leu cttccgacaa acaccaagac caatgacaat gatgatgaca acaacaatga tgatgatgag        468
aacgataact gcaatgaacg agactgatga ctctcgtgtg gtgtttggtc cttcacatgg        528
gtggtgggag tggttacaca aaacagaaaa aagaaaaaat acaaatatta aaaaagggag        588
agtaaaaaat gaaaaaaatc ccgtctgaaa catgtccact ttaatgtata attaattcat        648
caactaatta actcgccaat taattgtgca tcagcttaat gtctgtcctt tgataatctc        708
agacaatgtt ttgtggaata aatattcga tctctgccaa aaaaaaaaaa aaaaaaaaaa        768
aa                                                                      770
```

<210> SEQ ID NO 4
<211> LENGTH: 89
<212> TYPE: PRT
<213> ORGANISM: Octopus vulgaris

<400> SEQUENCE: 4

```
Met Ser Ala Thr Ala Ser Thr Thr Ser Ser Arg Lys Met Ala Phe Phe
1               5                   10                  15

Ile Phe Ser Met Leu Leu Leu Ser Leu Cys Leu Gln Thr Gln Ala Gln
                20                  25                  30

Asn Tyr His Phe Ser Asn Gly Trp His Pro Gly Gly Lys Arg Ser Ala
            35                  40                  45

Leu Ser Asp Ile Gln Cys His Phe Arg Gln Gln Thr Lys Ala Leu Ile
    50                  55                  60

Glu Lys Ile Leu Asp Glu Glu Ile Asn Arg Ile Ile Thr Thr Cys Thr
65                  70                  75                  80

Gly Pro Val Asn Glu Ile Ala Asp Leu
                85
```